United States Patent [19]

Paust et al.

[11] 4,212,827

[45] Jul. 15, 1980

[54] MANUFACTURE OF CANTHAXANTHIN

[75] Inventors: Joachim Paust, Neuhofen; Joachim Schneider; Hagen Jaedicke, both of Ludwigshafen, all of Fed. Rep. of Germany

[73] Assignee: BASF Aktiengesellschaft, Fed. Rep. of Germany

[21] Appl. No.: 841,697

[22] Filed: Oct. 13, 1977

Related U.S. Application Data

[63] Continuation-in-part of Ser. No. 705,992, Jul. 16, 1976, abandoned.

[30] Foreign Application Priority Data

Aug. 5, 1975 [DE] Fed. Rep. of Germany ....... 2534805

[51] Int. Cl.$^2$ ............................................. C07C 45/02
[52] U.S. Cl. .................................. 568/347; 568/348; 568/363; 568/364
[58] Field of Search ..................................... 260/586 P

[56] References Cited

U.S. PATENT DOCUMENTS

| | | | |
|---|---|---|---|
| 2,870,197 | 1/1959 | Isler et al. | 260/586 P |
| 2,871,267 | 1/1959 | Petracek et al. | 260/586 P |
| 3,646,149 | 2/1972 | Morel | 260/586 P |
| 3,790,635 | 2/1974 | Morel | 260/586 P |

OTHER PUBLICATIONS

Sidgwick, The Chemical Elements & Their Compounds, vol. II, pp. 1225–1239 (1952).
Petrachek et al., (II) J.A.C.S., vol. 78, pp. 1427–1433 (1956).

*Primary Examiner*—Norman Morgenstern
*Assistant Examiner*—James H. Reamer
*Attorney, Agent, or Firm*—Keil & Witherspoon

[57] ABSTRACT

Process for the manufacture of canthaxanthin by oxidizing β-carotene, retro-dehydro-carotene or echinenone with a salt of chloric or bromic acid in the presence of a catalyst and of an inert diluent or solvent.

15 Claims, No Drawings

MANUFACTURE OF CANTHAXANTHIN

This application is a continuation-in-part of application Ser. No. 705,992, which was filed on July 16, 1976 now abandoned.

The present invention relates to a process for the manufacture of canthaxanthin by oxidizing β-carotene, retro-dehydro-carotene or echinenone.

The product canthaxanthin is one of the carotinoid ketones and is essentially used as a food dye and as an additive for animal feeds.

The manufacture of canthaxanthin by oxidizing β-carotene or retro-dehydro-carotene with ammonium metaperiodate or an alkali metal metaperiodate has been disclosed (German Pat. No. 1,793,308). The reaction takes place in a two-phase system of water and an inert water-immiscible solvent, in the presence of a catalyst, eg. iodine, bromine or an oxide of an element of group Va, VIa, VIIa or VIII of the period table. The essential disadvantages of this process are the low yield, which varies between 17 and 38%, and the high cost of the metaperiodate used as the oxidizing agent.

We have found a process for the manufacture of canthaxanthin by oxidizing β-carotene, retro-dehydro-carotene or echinenone, wherein the oxidation is carried out with a salt of chloric acid or of bromic acid in the presence of chlorine, bromine or iodine or of an oxide or oxo-acid of selenium or of an element of group Va, VIa or VIIa of the periodic table, or a salt of such an oxo-acid, or of an oxide of an element of group VIII of the periodic table as a catalyst, and in the presence of an inert diluent or solvent, at from 0° to 50° C.

Essential advantages of the process according to the invention over the conventional process are the yield, which is increased by a factor of two, and the ready availability and low price of the oxidizing agents.

The starting materials are used in the form of dilute solutions, or of suspensions in a diluent, for the oxidation. Advantageously, solutions containing from 1 to 10 g of starting material per liter of an inert, readily volatile, water-immiscible solvent, or suspensions of starting material in a diluent, in which suspensions the amount of starting material per liter of diluent can be substantially greater, are used.

Suitable diluents or solvents are chlorinated aliphatic hydrocarbons, eg. chloroform, methylene chloride, 1,1-dichloroethane, 1,2-dichloroethane, 1,1,2-trichloroethane, 1,1,2,2-tetrachloroethane, 1,2-dichloroethylene, 1,1,2-trichloroethylene, aromatic hydrocarbons, eg. benzene, toluene, nitrobenzene or chlorobenzene, dialkyl ethers, eg. diethyl ether and di-n-propyl ether, and carbon disulfide. Chloroform, methylene chloride and nitrobenzene are particularly suitable solvents. Mixtures of these diluents or solvents can also be used.

Suitable oxidizing agents are salts of chloric acid or of bromic acid, especially the alkaline earth metal salts, alkali metal salts or ammonium salts, or the free acid. These are advantageously added to the reaction mixture in the form of aqueous solutions of from 5 to 50% strength by weight. The molar ratio of oxidizing agent to starting material is from 1:1 to 100:1 and preferably from 1:1 to 20:1. Using a more than 100-fold molar excess of oxidizing agent has not effect on the reaction.

The oxidation is catalyzed by chlorine, bromine or iodine or by an oxide or oxo-acid of selenium or of an element of group Va, VIa or VIIa of the periodic table or by a salt of such an oxo-acid or by an oxide of an element of group VIII of the periodic table. Examples of suitable catalysts are selenium dioxide, selenous acid and its salts, selenic acid and its salts, vanadium pentoxide, vanadates, polyvanadic acid and their salts, heteropolyacids of vanadium, especially with the elements tungsten, molybdenum and phosphorus, and their salts, molybdenum trioxide, molybdates, especially ammonium molybdate, polymolybdates, heteropolyacids of molybdenum, especially with the elements vanadium or phosphorus, tungsten trioxide, tungstates, polytungstic acids and their salts, heteropolyacids of tungsten, especially with the elements vanadium and phosphorus, and their salts, manganese dioxide, nickel oxide and osmium tetroxide. Bromine, iodine and osmium tetroxide are preferred catalysts. Iodine is a particularly suitable catalyst.

The catalyst is added in the pure form or in solution, eg. in the solvent which has been used to dissolve the starting material, or in water. The catalyst can also be formed in situ. The amount of catalyst is advantageously from 0.1 to 10% by weight, preferably from 1 to 5% by weight, based on starting material.

Because of the sensitivity of the compounds to heat, the oxidation is carried out at low temperatures; suitable temperatures are from 0° to 50° C., preferbly from 15° to 30° C.

The reaction takes place in a pH range extending from strongly acid values to pH 13. A pH of from 2 to 6 is preferred. Acids, eg. sulfuric acid, hydrochloric acid or acetic acid, or buffer mixtures, are used to bring the pH to the desired value.

The reaction time is from 1 to 250 hours, depending on the conditions chosen. In an advantageous embodiment, less than 20 hours are required to obtain an optimum yield of canthaxanthin.

To prevent oxidation of the canthaxanthin by atmospheric oxygen, the reaction is preferably carried out under an inert gas atmosphere. Inert gases suitable for use under the reaction conditions are argon, neon, helium, carbon dioxide and especially nitrogen.

In a preferred embodiment of the process, an aqueous solution of the oxidizing agent is added to a solution or a suspension of the starting material in a water-immiscible diluent or solvent which is inert under the reaction conditions, under an inert gas atmosphere. The aqueous phase is then brought to the desired pH by means of an acid or a buffer mixture. After adding the catalyst in the form of a solid or a solution, the reaction mixture is stirred until a check, made by thin layer chromatography using conventional methods, shows that only canthaxanthin remains present.

Canthaxanthin can either be precipitated by direct addition of methanol or ethanol to the organic phase or can be isolated by washing the organic phase with water, drying it and stripping off the diluent or solvent under reduced pressure. To achieve complete crystallization, ethanol or methanol is then added to the crude canthaxanthin. After a short time, the canthaxanthin can be separated off. This can be followed by an isomerizing treatment.

EXAMPLE 1

2 g of sodium chlorate, dissolved in 20 ml of water, are added to 1 g of β-carotene in 100 ml of chloroform, under a nitrogen atmosphere. The pH of the aqueous phase was brought to 3 with sulfuric acid. 15 mg of solid iodine are added and the mixture is stirred for 36 hours at 25° C. The organic phase is then washed with three 75 ml portions of water and is dried, and the solvent, apart from a small residual amount, is stripped off under reduced pressure. The oily residue is stirred with 50 ml of methanol and after 12 hours 0.74 g of canthaxanthin, having an all-trans content of 82% is isolated. Yield, 69.5%.

EXAMPLE 2

10 g of β-carotene are dissolved in 500 ml of chloroform under a nitrogen atmosphere, and 60 g of sodium chlorate in 80 ml of water are added. The pH of the aqueous phase was brought to 3–4 with glacial acetic acid. 200 mg of iodine, dissolved in 100 ml of chloroform, are then added and the mixture is stirred for 20 hours at 25° C. The organic phase is then washed with four 200 ml portions of water and is dried, and the solvent is stripped off under reduced pressure. 500 ml of ethanol are added to the oily residue and the mixture is left to stand for 25 hours at −10° C. 8.2 g of crude canthaxanthin of 80.5% purity are obtained by filtration. Yield, 78.5%.

EXAMPLE 3

1 g of β-carotene is dissolved in 100 ml of methylene chloride under a nitrogen atmosphere, and 10 g of sodium chlorate, dissolved in 20 ml of water (pH 7) are added. After adding 10 mg of iodine, the mixture is stirred for 5 days at 30° C. The UV spectrum indicates a canthaxanthin content of 56%.

EXAMPLE 4

10 g of β-carotene are dissolved in 1 l of methylene chloride under a nitrogen atmosphere and treated with 50 g of sodium chlorate in 200 ml of water. The pH of the aqueous phase is 2–3. After adding 200 mg of iodine, the mixture is stirred for 2 days at 25° C., the organic phase is then washed with four 200 ml portions of water and is dried, and the solvent is removed. 500 ml of ethanol are added to the residue and after the mixture has stood for 2 hours, the product is filtered off. Yield, 7.8 g of pure canthaxanthin, corresponding to 73.5%.

EXAMPLE 5

2.5 g of β-carotene are dissolved in 250 ml of methylene chloride under a nitrogen atmosphere and a solution of 3 g of potassium bromate in 50 ml of water is added. 50 mg of iodine are then added and the mixture is stirred for 24 hours at room temperature. Thereafter the aqueous phase is separated off and the organic phase is washed with two 100 ml portions of water and is dried with sodium sulfate. After filtration, the solvent is stripped off under reduced pressure and the oily residue is taken up in 500 ml of methanol. The mixture is stirred for 2 hours at 0° C. and 1.6 g of crude canthaxanthin, $E_1\ _{cm}^{1\%} = 1,650$ in cyclohexane at $\lambda_{max} = 464$ nm, are then filtered off.

EXAMPLE 6

100 mg of retro-dehydro-carotene are dissolved in 10 ml of chloroform under a nitrogen atmosphere, and 2 mg of iodine, dissolved in 1 ml of chloroform, are added, 100 mg of sodium chlorate in 1 ml of water are then added and the mixture is stirred for 4 hours at room temperature. The organic phase is then washed with water, dried and concentrated. After adding 20 ml of methanol, 79 mg of canthaxanthin, $E_1\ _{cm}^{1\%} = 1,850$ at $\lambda_{max} = 464$ nm in cyclohexane, precipitate.

EXAMPLE 7

100 mg of echinenone are dissolved in 10 ml of chloroform under a nitrogen atmosphere and are oxidized with 100 mg of sodium chlorate in 1 ml of water after having added 2 mg of iodine dissolved in 1 ml of chloroform. After stirring for 24 hours at −20° C., 67 mg of canthaxanthin having an all-trans content of 81% are obtained.

EXAMPLE 8

10 g of β-carotene are dissolved in 1 l of chloroform under a nitrogen atmosphere and 50 g of sodium chlorate, dissolved in 60 ml of water, are added. The mixture is acidified with dilute sulfuric acid to pH 2-3 and 130 mg of elementary bromine are added as the catalyst. The mixture is then stirred for 5 days at room temperature. The organic phase is separated off, washed with a dilute sodium thiosulfate solution and with three 300 ml portions of water and dried, and the solvent is distilled off under reduced pressure. After precipitation with methanol, 7.65 g of canthaxanthin, $E_1\ _{cm}^{1\%} = 1,820$ at $\lambda_{max} = 465$ nm in cyclohexane, are obtained.

EXAMPLE 9

An aqueous solution of 10 g of sodium chlorate in 15 ml of water is added to a solution of 2.5 g of β-carotene in 200 ml of chloroform under a nitrogen atmosphere, and 100 mg of vanadium pentoxide are added. The mixture is then stirred for 200 hours at 20° C. and the organic phase is separated off and is washed with three 100 ml portions of water and dried; the solvent is then distilled off under reduced pressure, 100 ml of methanol are added to the residue and the mixture is stirred for 2 hours at −10° C. On filtration, 1.8 g of canthaxanthin, $E_1\ _{cm}^{1\%} = 1,200$ at $\lambda_{max} = 468$ nm in cyclohexane, are obtained.

EXAMPLE 10

Working under a nitrogen atmosphere, 5 g of β-carotene are dissolved in 500 ml of chloroform and a solution of 5 g of sodium chlorate in 20 ml of water is added. 225 mg of selenium dioxide are added as the catalyst and the mixture is stirred for 18 hours at 23° C. It is worked up as described in Example 9 and 4.0 g of canthaxanthin, $E_1\ _{cm}^{1\%} = 1,550$ at $\lambda_{max} = 467$ nm in cyclohexane, are obtained.

EXAMPLE 11

2 g of sodium chlorate, dissolved in 5 ml of water, are added to a solution of 1 g of β-carotene in 100 ml of chloroform under a nitrogen atmosphere. A solution of 10 mg of osmium tetroxide in 10 ml of carbon tetrachloride is added dropwise to the mixture. The batch is then stirred for 120 hours at room temperature, after which it is worked up as described in Example 9. 630 mg of canthaxanthin, $E_1\ _{cm}^{1\%} = 1,840$ at $\lambda_{max} = 466$ nm is cyclohexane, are obtained.

EXAMPLE 12

10 g of all-trans β-carotene are suspended in 250 ml of chloroform and an aqueous solution of 20 g of sodium chlorate and 0.4 g of sodium iodide are added. At 30° C., 0.00075 mole of $H_2SO_4$ in 20 ml of $H_2O$ is added dropwise continuously over 2 hours, whilst continuing to keep the temperature at about 30° C. After 3–4 hours, only canthaxanthin remains detectable by thin layer chromatography. The mixture is rendered alkaline with sodium hydroxide solution and the organic solution is washed repeatedly with water. The solvent is then distilled off under reduced pressure. 200 ml of methanol are added to the crude product and the mixture is boiled up briefly and then filtered. 8.7 g of canthaxanthin are obtained as the residue; purity 97 percent.

EXAMPLE 13

10 g of β-carotene are suspended in 150 ml of methylene chloride. 13 g of sodium chlorate in 100 ml of water, and 0.3 g of elementary iodine, are added. The mixture is heated at 40° C. for 3 hours, with vigorous stirring. The aqueous phase is separated off and the organic phase is washed repeatedly with dilute sodium carbonate solution and then with water, after which 1.3 l of methanol are added to it.

The methylene chloride is distilled off and the mixture is cooled and then filtered. 8.1 g of canthaxanthin are obtained; purity 96.8%.

We have also found that canthaxanthin is obtained by the oxidation of isozeaxanthin or 4'-hydroxyechinenone as starting materials with a salt of chloric acid or bromic acid.

When using isozeaxanthin or 4'-hydroxyechinenone as starting materials in the process according to the invention, there is a more rapid progress of the reaction in addition to the increased yield and ready availability and low price of the oxidizing agents.

These starting materials for the oxidation are used in the form of dilute solutions or suspensions in a diluent. The solutions contain the same range for the concentration of the starting material as described previously for β-carotene, retro-dehydro-carotene or echinenone as starting materials in the process according to the invention. Suitable diluents or solvents, oxidizing agents and catalysts and their respective amounts have likewise been described previously in connection with the latter mentioned starting materials.

The reaction is carried out at temperatures of from 0° to 100° C., preferably from 15° to 40° C.

The reaction takes place in a pH range extending from strongly acid values to pH 7. A pH of from 2 to 6 is preferred. Acids, e.g. sulfuric acid, hydrochloric acid or acetic acid, or buffer mixtures, are used to bring the pH to the desired value.

The reaction time is from 1 to 25 hours, depending on the conditions chosen. In an advantageous embodiment, less than 2 hours are required to obtain an optimum yield of canthaxanthin.

The reaction is preferably carried out under inert gas atmosphere as described previously for the reaction of β-carotene, retro-dehydro-carotene or echinenone as starting materials and the preferred embodiment for carrying out the process is likewise the same.

Canthaxanthin can either be precipitated by direct addition of methanol or ethanol to the organic phase or can be isolated by washing the organic phase with water, drying it and stripping off the diluent or solvent under reduced pressure. To achieve complete crystallization, ethanol or methanol is then added to the crude canthaxanthin. After a short time, the canthaxanthin can be separated. If desired, isomerization to give the desired alltrans form may be carried out in conventional manner, e.g. by heating the crude product in organic solvents such as alcohols, e.g. methanol, ethanol, butanol and isobutanol, or aliphatic hydrocarbons such as heptane, if desired with the addition of small amounts of iodine.

The following Examples are directed to the use of isozeaxanthin or 4'-hydroxyechinenone as starting materials for the oxidation according to the invention.

EXAMPLE 14

An aqueous solution of 3.2 g of sodium chlorate and 20 mg of sodium iodide, dissolved in 20 ml of water, is added to 500 mg of racemic isozeaxanthin dissolved in 50 ml of chloroform, the two-phase mixture is stirred thoroughly at room temperature, and 5 ml of 0.01N sulfuric acid is added. After an hour, the mixture is neutralized with dilute sodium carbonate solution, the phases are separated, and the organic phase is washed with water and dried over sodium sulfate. The solvent is distilled off under reduced pressure, 50 ml of heptane is added to the residue, and the whole is refluxed for 1 hour. After cooling, filtration gives 471 g (94% of theory) of canthaxanthin.

EXAMPLE 15

50 mg of sodium chlorate dissolved in 0.9 ml of water is added to 100 mg of 4'-hydroxyechinenone dissolved in 10 ml of methylene chloride. The solution is stirred at room temperature, and 3 ml of methylene chloride in which 1 mg of iodine is dissolved is dripped in over a period of 10 minutes. After a further 20 minutes 4 ml of water is added and the phases are separated. Thin layer chromatography shows canthaxanthin to be the only reaction product. The yield is determined by UV spectroscopy and is 81.3 mg of canthaxanthin.

EXAMPLE 16

1.5 g of sodium bromate dissolved in 20 ml of water is added to 1.5 g of isozeaxanthin dissolved in 250 ml of 1,2-dichloroethane. While stirring, 10 ml of 1,2-dichloroethane in which 30 mg of bromine is dissolved is dripped in over a period of 30 minutes. The pH of the aqueous phase is 5.6. After stirring for 1 hour at room temperature, the phases are separated, the 1,2-dichloroethane is washed with sodium bicarbonate solution and water and dried, and the solvent is distilled off under reduced pressure. 20 ml of methanol is added to the residue and the whole stirred for 10 minutes at 50° C. After cooling, filtration gives 1.36 g (92% of theory) of canthaxanthin.

EXAMPLE 17

1 g of isozeaxanthin, 20 ml of ethylene chloride, and 15 ml of water in which 0.5 g of sodium chlorate and 0.02 g of sodium iodide are dissolved, are heated to reflux temperature. While stirring, the mixture is acidified with 0.04 ml of 1N sulfuric acid. After 40 minutes' vigorous stirring and refluxing at 72° C., only canthaxanthin is detectable on the chromatogram. The aqueous phase is neutralized with dilute aqueous sodium bicarbonate solution, and the whole allowed to cool. The organic phase is separated and washed with a dilute solution of sodium bisulfite until free of iodine. The organic phase is washed again with 20 ml of water, and dried over magnesium sulfate, and the ethylene chloride is then distilled off under reduced pressure. 8 ml of isopropyl alcohol is added to the residue, and the whole is refluxed for 10 minutes before being allowed to stand for 10 hours at room temperature. Suction filtration gives 0.874 g (88% of theory) of canthaxanthin.

We claim:

1. A process for the manufacture of canthaxanthin by oxidizing β-carotene, retro-dehydro-carotene, echinenone, 4'-hydroxyechinenone or isozeaxanthin which comprises carrying out the oxidation with chloric or bromic acid or with a salt of chloric or bromic acid in a proportion of 1 to 100 moles of said acid or salt of said acid per mole of β-carotene, retro-dehydrocarotene, echinenone, 4'-hydroxyechinenone or isozeaxanthin, in the presence of bromine or iodine or of an oxide or oxo-acid of selenium or of an element of group Va, VIa or VIIa of the periodic table, or a salt of such an oxo-acid, or of an oxide of an element of group VIII of the periodic table as a catalyst, and in the presence of an inert diluent or solvent, at from 0° to 100° C.

2. A process as set forth in claim 1, wherein the oxidation is carried out with an alkali metal salt of chloric or bromic acid.

3. A process as set forth in claim 1, wherein the oxidation is carried out in the presence of iodine as the catalyst.

4. A process as set forth in claim 1, wherein the oxidation is carried out in the presence of a chlorinated aliphatic hydrocarbon as the diluent or solvent.

5. A process as set forth in claim 1, wherein the inert diluent or solvent is a chlorinated aliphatic hydrocarbon, aromatic hydrocarbon, dialkyl ether, carbon disulfide or mixtures thereof.

6. A process as set forth in claim 1, wherein the salts of chloric or bromic acids are the alkaline earth metal salts, alkali metal salts or ammonium salts.

7. A process as set forth in claim 1, wherein the oxide or oxo-acid or salt thereof of selenium or an element of group Va, VIa, or VIIa or oxide of an element of group VIII of the periodic table is selected from the group consisting of selenium dioxide, selenous acid and its salts, selenic acid and its salts, vanadium pentoxide, polyvanadic acid and their salts, heteropolyacids of vanadium with the elements tungsten, molybdenum and phosphorus and their salts, molybdenum trioxide, ammonium molybdate, polymolybdates, heteropolyacids of molybdenum with the elements vanadium or phosphorus, tungsten trioxide, polytunstic acids and their salts, heteropolyacids of tungsten with the elements vanadium and phosphorus and their salts, manganese dioxide, nickel oxide and osmium tetroxide as catalyst.

8. A process as set forth in claim 1, wherein the oxidation is carried out in the presence of bromine, iodine or osmium tetroxide as catalyst.

9. A process as set forth in claim 1, wherein the amount of catalyst is from 0.1 to 10% by weight based on starting material.

10. A process as set forth in claim 1, wherein the oxidation is carried out under an inert gas atmosphere.

11. A process as set forth in claim 1, wherein the chloric or bromic acid or salt of chloric or bromic acid is added in aqueous solutions of from 5 to 50% strength by weight.

12. A process as set forth in claim 1, wherein the oxidation takes place in a pH range up to pH 13.

13. A process as set forth in claim 1, wherein the oxidation takes place in a pH range up to 7.

14. A process as set forth in claim 1, wherein the oxidation takes place in a pH range from 2 to 6.

15. A process as set forth in claim 1, wherein the oxidation is carried out at a reaction time of from 1 to 250 hours.

* * * * *